(12) United States Patent
Zhao et al.

(10) Patent No.: US 11,254,962 B2
(45) Date of Patent: Feb. 22, 2022

(54) METHOD FOR PREPARING SALIDROSIDE

(71) Applicant: XI'AN RAINBOW BIO-TECH CO., LTD, Xi'an (CN)

(72) Inventors: Caihong Zhao, Shaanxi (CN); Jicheng Gui, Shaanxi (CN); Maodong Liu, Shaanxi (CN); Zhaolin Mao, Shaanxi (CN); Yingjun Geng, Shaanxi (CN); Langjun Cui, Shaanxi (CN)

( * ) Notice: Subject to any disclaimer, the term of this patent is extended or adjusted under 35 U.S.C. 154(b) by 0 days.

(21) Appl. No.: 17/041,427

(22) PCT Filed: Oct. 23, 2018

(86) PCT No.: PCT/CN2018/111448
§ 371 (c)(1),
(2) Date: Sep. 24, 2020

(87) PCT Pub. No.: WO2020/062373
PCT Pub. Date: Apr. 2, 2020

(65) Prior Publication Data
US 2021/0017560 A1   Jan. 21, 2021

(30) Foreign Application Priority Data
Sep. 26, 2018 (CN) .......................... 201811125532.2

(51) Int. Cl.
*C12P 7/22* (2006.01)
*C12P 19/44* (2006.01)
*C12N 11/087* (2020.01)
*C12N 9/42* (2006.01)
*C12N 11/14* (2006.01)

(52) U.S. Cl.
CPC ............ *C12P 19/44* (2013.01); *C12N 9/2445* (2013.01); *C12N 11/087* (2020.01); *C12N 11/14* (2013.01); *C12Y 302/01021* (2013.01)

(58) Field of Classification Search
CPC .......... C12P 19/44; C12P 7/22; C12N 11/087; C12N 9/2445; C12N 11/14; C12Y 302/01021
See application file for complete search history.

(56) References Cited

FOREIGN PATENT DOCUMENTS

| CN | 103642880 A | 3/2014 |
|---|---|---|
| CN | 103710412 A | 4/2014 |
| CN | 104911237 A | 9/2015 |

(Continued)

OTHER PUBLICATIONS

Chen et al., "Cross-linked enzyme aggregates of β-glucosidase from Prunus domestica seeds," Biotechnol Lett 34:1673-1678, 2012 (Year: 2012).*

(Continued)

*Primary Examiner* — Rosanne Kosson
*Assistant Examiner* — Trevor Logan Kane

(57) ABSTRACT

The present invention provides a method for preparing salidroside. The present invention uses β-glucoside and $CoFe_2O_4$ particles to form a cross-linked aggregate capable of effectively catalyzing the reaction of β-D-glucose and tyrosol, thereby increasing the yield of the salidroside. The steps of the preparation method of the present invention are simple and short, and the method is easy to operate and readily applicable to industrial production.

10 Claims, 1 Drawing Sheet

(56) References Cited

FOREIGN PATENT DOCUMENTS

| CN | 106222218 A | 12/2016 |
| CN | 109280681 A | 1/2019 |

OTHER PUBLICATIONS

Wang et al., "Study on synthesis of salidroside using immobilization β-glucosidase," Shengwu Jishu 19(1):68-70, 2009 (Year: 2009).*
International search report of PCT/CN2018/111448.

* cited by examiner

METHOD FOR PREPARING SALIDROSIDE

FIELD

The present invention belongs to the field of salidroside preparation, and particularly relates to a method for preparing salidroside.

BACKGROUND

Salidroside, with the chemical name being 2-(4-hydroxyphenyl)ethyl-β-D-glucoside and the CAS being 10338-51-9, is a compound extracted from dried roots and rhizomes or dried whole herb of rhodiola crenulata of crassulaceae plants and has the effects of preventing tumors, enhancing an immunologic function, delaying senescence, resisting fatigue, anoxia and radiation, bidirectionally regulating nerves centralis, repairing and protecting organisms and the like.

At present, the salidroside can be extracted from plants, but the extraction process is tedious and the extraction rate is low. In addition, the salidroside can be synthesized by means of a chemical method and an enzyme catalysis method; however, the chemical synthesis method needs to adopt a chemical reagent, which is high in toxicity and environment-unfriendly. The enzymatic synthesis for the salidroside has the characteristics of mild reaction conditions, high stereoselectivity, simple reaction process, less environmental pollution and the like, and shows certain superiority.

At present, free β-glucosidase is mostly used for synthesizing the salidroside, the stability is poor, and particularly in some organic solvent medium reaction systems with high hydrophilicity, great reduction on the stability and catalytic activity of the free enzymes will be caused. The patent application with the application number of 201711141952.5 discloses a β-glucosidase catalyst, the catalyst is used for catalyzing β-D-glucose and an n-butyl alcohol mechanism to carry out a reverse hydrolysis reaction to synthesize n-butyl-β-D-glucoside, then a glucoside conversion reaction is carried out under the catalysis of the β-glucosidase catalyst by taking the n-butyl-β-D-glucoside as a glycosyl donor to synthesize the salidroside, but the highest yield is only 35%, which is still unsatisfactory.

In view of the above, the present invention provides a method for preparing the salidroside so as to improve the yield of the salidroside.

SUMMARY

For the problems in the prior art, the object of the present invention is to provide a method for preparing salidroside. In order to achieve the above object, the present invention adopts the following technical solution:

the method for preparing the salidroside comprises the following steps:

(1) adding β-glucosidase into a phosphate-citric acid buffer solution, adding polyacrylamide cross-linked hollow $CoFe_2O_4$ particles, adding a settling agent, glutaraldehyde and sodium borohydride after oscillating, oscillating, centrifuging same at 320-480 rpm for 5-10 min, sending same into a thermostatic water bath at 40-45° C., keeping the temperature and stirring same for 1-2 h, discharging, and collecting precipitate to obtain a β-glucosidase cross-linked aggregate;

(2) adding β-D-glucose and tyrosol into a solvent, adding the buffer solution and the β-glucosidase cross-linked aggregate obtained in the step (1), and reacting to obtain a reaction solution; and (3) filtering the reaction solution obtained in the step (2), and carrying out reduced pressure distillation on a filtrate to obtain a crude product; and recrystallizing the crude product to obtain the salidroside.

A method for preparing the polyacrylamide cross-linked hollow $CoFe_2O_4$ particles comprises the following steps:

(1) adding 1-2 parts by weight of ammonium persulfate into deionized water which is 20-30 times of the weight of the ammonium persulfate, and uniformly stirring same; and (2) adding 40-45 parts by weight of methyl methacrylate into the deionized water which is 5-8 times of the weight of the methyl methacrylate, uniformly stirring same, feeding same into a reaction kettle, introducing nitrogen, regulating the temperature of the reaction kettle to 60-75° C., keeping the temperature and stirring same for 3-5 h, discharging, cooling, adding 300-500 parts by weight of 0.8-1 mol/l ferric nitrate solution and 200-240 parts by weight of 1.7-2 mol/l cobalt nitrate solution, uniformly stirring same, adding citric acid, regulating pH to 3-4, heating same with steam at 100-110° C. until water is dried, discharging, feeding same into a sintering furnace, calcining same at 500-550° C. for 2-3 h, discharging and cooling, feeding same into an acetone solution, soaking at 60-70° C. for 100-110 min, discharging, drying at normal temperature, blending same with 0.3-0.4 part by weight of sodium persulfate, 20-25 parts by weight of acrylamide and 5-7 parts by weight of calcium chloride, uniformly stirring same, adding the mixture into the deionized water which is 10-20 times of the weight of the mixture, feeding same into the reaction kettle, introducing the nitrogen, regulating the temperature of the reaction kettle to 70-80° C., keeping the temperature and stirring same for 3-5 h, discharging, feeding a product into a drying oven, carrying out vacuum drying at 90-100° C. for 3-5 h, discharging and cooling to obtain the polyacrylamide cross-linked hollow $CoFe_2O_4$ particles.

In the above preparation method, as a preferred embodiment, in the step (1), a mass ratio of the β-glucosidase to the polyacrylamide cross-linked hollow $CoFe_2O_4$ particles is 1:(0.5-1.2) (such as 1:0.6, 1:0.7, 1:0.8, 1:0.9, 1:1.1).

In the above preparation method, as a preferred embodiment, in the step (1), the pH value of the phosphate-citric acid buffer solution is 5.0-6.0.

In the above preparation method, as a preferred embodiment, in the step (2), the solvent is dioxane, tetrahydrofuran, dimethyl sulfoxide or dimethyl formamide.

In the above preparation method, as a preferred embodiment, in the step (2), a molar ratio of the β-D-glucose to the tyrosol is 1:(1-1.5) (such as 1:1.1, 1:1.2, 1:1.3, 1:1.4).

In the above preparation method, as a preferred embodiment, in the step (2), the buffer solution is a phosphate-citric acid buffer solution, a sodium citrate-citric acid buffer solution, a sodium dihydrogen phosphate-citric acid buffer solution, a sodium dihydrogen phosphate-phosphoric acid buffer solution, a disodium hydrogen phosphate-citric acid buffer solution or a disodium hydrogen phosphate-phosphoric acid buffer solution; and preferably, the pH value of the buffer solution is 5.0-6.0.

In the above preparation method, as a preferred embodiment, in the step (2), the reaction temperature is 25-70° C. (such as 30° C., 40° C., 50° C., and 60° C.), and the reaction time is 6-16 h (such as 7 h, 8 h, 9 h, 10 h, 11 h, 12 h, 13 h, 14 h, and 15 h).

In the above preparation method, as a preferred embodiment, in the step (3), the recrystallization solvent is n-hexane-methanol or n-hexane-ethanol.

The principle for preparing the salidroside is as follows: firstly, the glutaraldehyde is used as a cross-linking agent, the dioxane is used as a settling agent, a ferromagnetic material is used as a core, and covalent bonds of the ferromagnetic material are combined with enzyme molecules, such that immobilized enzymes with certain magnetic cores are formed, and the immobilization stability of the β-glucosidase is further improved; the selected magnetic material is the hollow $CoFe_2O_4$ particles, more stable attachment sites can be provided for the immobilized enzymes, and the immobilization capacity for the β-glucosidase can be expanded, such that the catalytic efficiency is further improved, and the yield is increased; the obtained hollow $CoFe_2O_4$ particles are subjected to cross-linking modification by means of polyacrylamide, calcium ions are introduced for doping in the cross-linking process, the calcium ions have a good adsorption and chelation effect on the β-glucosidase at the water bath temperature, through cross-linking of the polyacrylamide, the calcium ion doping stability can be improved, the polyacrylamide also has a certain adsorption effect and can achieve a synergistic effect with the calcium ions, and the polyacrylamide has a very good flocculating settling effect and is synergistic with the settling agent to increase a settling rate, such that the yield of the β-glucosidase cross-linked aggregate is increased;

experiments find that when the magnetic material $CoFe_2O_4$ particles are combined with the β-glucosidase of the present invention, the β-glucosidase cross-linked aggregate can be obtained at a high yield, and the β-glucosidase cross-linked aggregate formed by taking the $CoFe_2O_4$ particles as a core is good in dispersity, small in size, and high in activity and catalytic efficiency when the salidroside is catalytically synthesized, such that the yield of the salidroside is further improved; and in addition, the β-glucosidase of the present invention is also resistant to high temperature, such that an enzyme catalytic reaction can be carried out under a high-temperature condition, and the yield of the salidroside is further improved.

Compared with the prior art, the present invention has the following technical effects:

at present, the β-glucosidase on the market mainly comes from microbial fermentation or is extracted from plants, and if free enzymes are directly used in production, the product cost will be increased due to the fact that the stability of the enzymes is low and the enzymes cannot be reused. Due to the fact that the β-glucosidase is expensive, the β-glucosidase is immobilized on a carrier for repeated use by adopting an immobilization technology, such that the purposes of simplifying the process and reducing the cost can be achieved. The present invention uses the β-glucoside and the $CoFe_2O_4$ particles to form the cross-linked aggregate capable of effectively catalyzing the reaction between the β-D-glucose and the tyrosol, thereby increasing the yield of the salidroside, and the immobilized enzyme cross-linked aggregate of the present invention has the advantages of being high in storage stability, easy to separate and recycle, capable of being repeatedly used and the like. The steps of the method for preparing the salidroside of the present invention are simple and short, and the method is easy to operate and readily applicable to industrial production.

BRIEF DESCRIPTION OF THE DRAWINGS

The present invention is further explained below in conjunction with accompanying drawings.

DETAILED DESCRIPTION OF THE EMBODIMENTS

Figure 1:
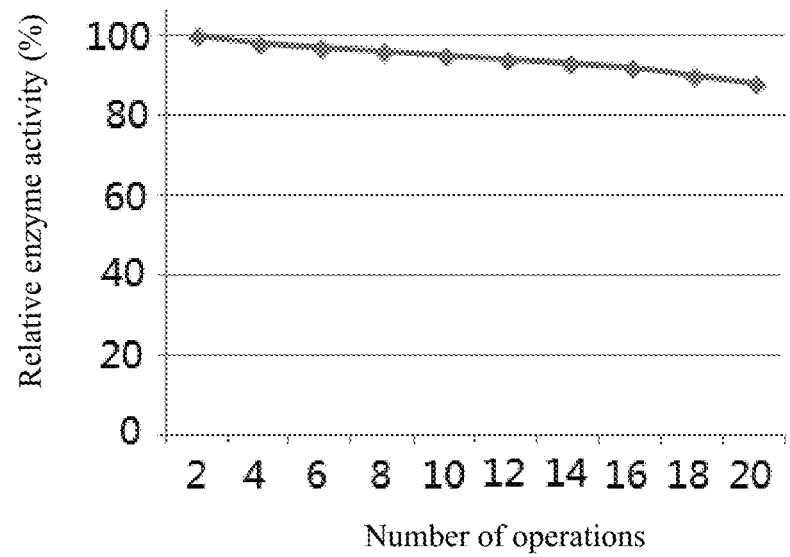
FIG. 1 is an operational stability test diagram of immobilized enzymes of an embodiment of the present invention.

The present invention is described in detail below by means of specific embodiments, but these exemplary execution modes are not intended to constitute any limitation of any form to the actual scope of protection of the present invention.

Prune seed β-glucosidase and black plum seed β-glucosidase used in the following embodiments are purchased from the market, other chemical reagents and drugs are also commercially available products, and instruments not specifically labeled are conventional instruments.

Embodiment 1

(1) adding 1 g of the prune seed β-glucosidase into a phosphate-citric acid buffer solution with the pH value of 5.0, adding 0.5 g of polyacrylamide cross-linked hollow $CoFe_2O_4$ particles, adding a proper amount of dioxane, glutaraldehyde and sodium borohydride after oscillating, oscillating, centrifuging same at 320 rpm for 6 min, feeding same into a thermostatic water bath at 40° C., keeping the temperature and stirring same for 1 h, discharging, and collecting precipitates to obtain 1.2 g of a prune seed β-glucosidase cross-linked aggregate;

(2) adding β-D-glucose (1 mmol, 180 mg) and tyrosol (1.2 mmol, 165.6 mg) into 10 ml of the dioxane, adding a sodium citrate-citric acid buffer solution with the pH value of 6 and 50 mg of the prune seed β-glucosidase cross-linked aggregate obtained in the step (1), and reacting at 60° C. for 12 h to obtain a reaction solution; and (3) filtering the reaction solution obtained in the step (2), and carrying out reduced pressure distillation on a filtrate to obtain a crude product; and recrystallizing the crude product by using n-hexane-methanol to obtain 210 mg of salidroside, wherein the yield is 70%.

Embodiment 2

(1) adding 0.5 g of the prune seed β-glucosidase into a phosphate-citric acid buffer solution with the pH value of 5.5, adding 0.5 g of polyacrylamide cross-linked hollow $CoFe_2O_4$ particles, adding a proper amount of dioxane, glutaraldehyde and sodium borohydride after oscillating, oscillating, centrifuging same at 360 rpm for 8 min, feeding same into a thermostatic water bath at 45° C., keeping the temperature and stirring same for 1 h, discharging, and collecting precipitates to obtain 0.8 g of a prune seed β-glucosidase cross-linked aggregate;

(2) adding β-D-glucose (2 mmol, 360 mg) and tyrosol (2.6 mmol, 358.8 mg) into 25 ml of the dioxane, adding a sodium dihydrogen phosphate-citric acid buffer solution with the pH value of 5 and 100 mg of the prune seed β-glucosidase cross-linked aggregate obtained in the step (1), and reacting at 70° C. for 6 h to obtain a reaction solution; and (3) filtering the reaction solution obtained in the step (2), and carrying out reduced pressure distillation on a filtrate to obtain a crude product; and recrystallizing the crude product by using n-hexane-methanol to obtain 432 mg of salidroside, wherein the yield is 72%.

Embodiment 3

(1) adding 0.5 g of the black plum seed β-glucosidase into a phosphate-citric acid buffer solution with the pH value of 6.0, adding 0.3 g of polyacrylamide cross-linked hollow $CoFe_2O_4$ particles, adding a proper amount of dioxane, glutaraldehyde and sodium borohydride after oscillating, oscillating, centrifuging same at 400 rpm for 8 min, feeding same into a thermostatic water bath at 42° C., keeping the temperature and stirring same for 1 h, discharging, and collecting precipitates to obtain 0.6 g of a black plum seed β-glucosidase cross-linked aggregate;

(2) adding β-D-glucose (0.5 mmol, 90 mg) and tyrosol (0.7 mmol, 96.6 mg) into 10 ml of the dioxane, adding a sodium citrate-citric acid buffer solution with the pH value of 6 and 20 mg of the black plum seed β-glucosidase cross-linked aggregate obtained in the step (1), and reacting at 50° C. for 10 h to obtain a reaction solution; and (3) filtering the reaction solution obtained in the step (2), and carrying out reduced pressure distillation on a filtrate to obtain a crude product; and recrystallizing the crude product by using n-hexane-ethanol to obtain 103.5 mg of salidroside, wherein the yield is 69%.

Embodiment 4

(1) adding 0.5 g of the black plum seed β-glucosidase into a phosphate-citric acid buffer solution with the pH value of 5.5, adding 0.6 g of polyacrylamide cross-linked hollow $CoFe_2O_4$ particles, adding a proper amount of dioxane, glutaraldehyde and sodium borohydride after oscillating, oscillating, centrifuging same at 380 rpm for 8 min, feeding same into a thermostatic water bath at 41° C., keeping the temperature and stirring same for 1.5 h, discharging, and collecting precipitate to obtain 0.9 g of a black plum seed β-glucosidase cross-linked aggregate;

(2) adding β-D-glucose (1 mmol, 180 mg) and tyrosol (1.5 mmol, 207 mg) into 20 ml of the dioxane, adding a sodium citrate-citric acid buffer solution with the pH value of 5.5 and 40 mg of the black plum seed β-glucosidase cross-linked aggregate obtained in the step (1), and reacting at 40° C. for 10 h to obtain a reaction solution; and (3) filtering the reaction solution obtained in the step (2), and carrying out reduced pressure distillation on a filtrate to obtain a crude product; and recrystallizing the crude product by using n-hexane-ethanol to obtain 195 mg of salidroside, wherein the yield is 65%.

Embodiment 5

(1) adding 0.5 g of the black plum seed β-glucosidase into a phosphate-citric acid buffer solution with the pH value of 5.5, adding 0.4 g of polyacrylamide cross-linked hollow $CoFe_2O_4$ particles, adding a proper amount of dioxane, glutaraldehyde and sodium borohydride after oscillating, oscillating, centrifuging same at 380 rpm for 8 min, feeding same into a thermostatic water bath at 44° C., keeping the temperature and stirring same for 2 h, discharging, and collecting precipitates to obtain 0.6 g of a black plum seed β-glucosidase cross-linked aggregate;

(2) adding β-D-glucose (1 mmol, 180 mg) and tyrosol (1.2 mmol, 165.6 mg) into 15 ml of the dioxane, adding a sodium citrate-citric acid buffer solution with the pH value of 6 and 80 mg of the black plum seed β-glucosidase cross-linked aggregate obtained in the step (1), and reacting at 30° C. for 10 h to obtain a reaction solution; and (3) filtering the reaction solution obtained in the step (2), and carrying out reduced pressure distillation on a filtrate to obtain a crude product; and recrystallizing the crude product by using n-hexane-ethanol to obtain 177 mg of salidroside, wherein the yield is 68%.

COMPARATIVE EXAMPLE 1 (WITHOUT MAGNETIC PARTICLES ADDED)

(1) adding β-D-glucose (2 mmol, 360 mg) and tyrosol (2.6 mmol, 358.8 mg) into 25 ml of the dioxane, adding a sodium dihydrogen phosphate-citric acid buffer solution with the pH value of 5 and 100 mg of prune seed β-glucosidase, and reacting at 50° C. for 6 h to obtain a reaction solution; and (2) filtering the reaction solution obtained in the step (1), and carrying out reduced pressure distillation on a filtrate to obtain a crude product; and recrystallizing the crude product by using n-hexane-methanol to obtain 252 mg of salidroside, wherein the yield is 42%.

COMPARATIVE EXAMPLE 2 (WITH ORDINARY MAGNETIC PARTICLES ADDED)

(1) adding 0.5 g of the black plum seed β-glucosidase into a phosphate-citric acid buffer solution with the pH value of 5.5, adding 0.4 g of $CoFe_2O_4$ particles, adding a proper amount of dioxane, glutaraldehyde and sodium borohydride after oscillating, oscillating, centrifuging same at 380 rpm for 8 min, and collecting precipitates to obtain 0.6 g of a black plum seed β-glucosidase cross-linked aggregate;

(2) adding β-D-glucose (1 mmol, 180 mg) and tyrosol (1.2 mmol, 165.6 mg) into 15 ml of the dioxane, adding a sodium citrate-citric acid buffer solution with the pH value of 6 and 80 mg of the black plum seed β-glucosidase cross-linked aggregate obtained in the step (1), and reacting at 30° C. for 10 h to obtain a reaction solution; and (3) filtering the reaction solution obtained in the step (2), and carrying out reduced pressure distillation on a filtrate to obtain a crude product; and recrystallizing the crude product by using n-hexane-ethanol to obtain 177 mg of salidroside, wherein the yield is 47%.

COMPARATIVE EXAMPLE 3 (WITH HOLLOW MAGNETIC PARTICLES NOT CROSS-LINKED WITH POLYACRYLAMIDE ADDED)

(1) adding 0.5 g of the black plum seed β-glucosidase into a phosphate-citric acid buffer solution with the pH value of 5.5, adding 0.4 g of hollow $CoFe_2O_4$ particles, adding a proper amount of dioxane, glutaraldehyde and sodium borohydride after oscillating, oscillating, centrifuging same at 380 rpm for 8 min, and collecting precipitates to obtain 0.6 g of a black plum seed β-glucosidase cross-linked aggregate;

(2) adding β-D-glucose (1 mmol, 180 mg) and tyrosol (1.2 mmol, 165.6 mg) into 15 ml of the dioxane, adding a sodium citrate-citric acid buffer solution with the pH value of 6 and 80 mg of the black plum seed β-glucosidase cross-linked aggregate obtained in the step (1), and reacting at 30° C. for 10 h to obtain a reaction solution; and (3) filtering the reaction solution obtained in the step (2), and carrying out reduced pressure distillation on a filtrate to obtain a crude product; and recrystallizing the crude product by using n-hexane-ethanol to obtain 177 mg of salidroside, wherein the yield is 59%.

A method for preparing hollow $CoFe_2O_4$ particles comprises:

(1) adding 1 part by weight of ammonium persulfate into deionized water which is 20 times of the weight of the ammonium persulfate, and uniformly stirring same; and (2) adding 40 parts by weight of methyl methacrylate into the deionized water which is 5-8 times of the weight of the methyl methacrylate, uniformly stirring same, feeding same into a reaction kettle, introducing nitrogen, regulating the temperature of the reaction kettle to 60-75° C., keeping the temperature and stirring same for 3-5 h, discharging, cooling, adding 300 parts by weight of 0.8 mol/l a ferric nitrate solution and 200 parts by weight of a 1.7-2 mol/l cobalt nitrate solution, uniformly stirring same, adding citric acid, regulating pH to 3, heating same with steam at 100° C. until water is dried, discharging, feeding same into a sintering furnace, calcining same at 500° C. for 2 h, discharging and cooling, feeding same into an acetone solution, soaking at 60° C. for 100 min, discharging, carrying out vacuum drying at 90° C. for 3 h, discharging and cooling to obtain the hollow $CoFe_2O_4$ particles.

TEST EXAMPLE

Enzyme activity determination: placing 1.0 mL (1 mg/mL) of an enzyme solution or 0.2 g of immobilized enzymes in a test tube, and adding 0.5 mL of an acetic acid buffer solution with pH 5.0 and 0.5 mL of a geniposide standard solution (1 mg/mL), wherein free enzymes and the immobilized enzymes react at a constant temperature of 50° C. and 60° C. for 30 min respectively; after the completion of the enzymatic hydrolysis reaction of the free enzymes, immediately carrying out boiling water bath for 10 min to deactivate the enzymes; and immediately taking 0.5 mL of supernatant correspondingly, adding 0.5 mL of distilled water and 1 mL of a DNS reagent, carrying out boiling water bath for 5 min, flushing the test tube with water to rapidly cool the reaction solutions, diluting same to 10 mL, and measuring a light absorption value $OD_{540\ nm}$. The same quantity of heat-inactivated free enzymes and immobilized enzymes are used for blank control. Enzyme activity definition: in the above conditions, the quantity of enzymes required to hydrolyze within each hour to produce 1 μmol of glucose is an enzyme activity unit (U). Relative enzyme activity is calculated by taking the highest enzyme activity as 100%.

1. Stability Experiment of the Immobilized Enzymes

The immobilized enzymes (a β-glucosidase cross-linked aggregate) are stored in a sealed manner in a refrigerator at 4° C. and regularly sampled every 5 d to measure the enzyme activity of the immobilized enzymes. Then the immobilized enzymes subjected to the first reaction is washed clean with an acetic acid buffer solution, the enzymatic hydrolysis reaction is carried out again under the same conditions, such a process is repeated 5 times, and the enzyme activity of the immobilized enzymes is measured every time.

TABLE 1

| Storage stability of immobilized enzymes | | | | | | | |
|---|---|---|---|---|---|---|---|
| Relative enzyme | Time (d) | | | | | | |
| activity (%) | 1 | 5 | 10 | 15 | 20 | 25 | 30 |
| Immobilized enzyme 4° C. | 100 | 99.7 | 99.4 | 99.1 | 98.7 | 98.2 | 97.5 |

As can be seen from Table 1, the enzyme activity of the immobilized enzymes is maintained at a high level within 30 d, which shows that the immobilized enzymes can be stored at 4° C., and the enzyme activity of the immobilized β-glucosidase is kept stable within a month, which shows that the stability of the immobilized enzymes is good.

2. Operational Stability of the Immobilized Enzymes

The enzymatic hydrolysis reaction is carried out, 20 batches of operation is continuously carried out under the same conditions, the enzyme activity of the enzymes is measured, and with the first-batch enzyme activity as 100%, the relative activity is calculated, wherein the result is shown in FIG. 1.

As can be seen in FIG. 1, the immobilized enzymes have good operational stability, the relative enzyme activity is still higher than 90% after continuous use of 18 batches, and the relative enzyme activity is still 85% or above after continuous use of 20 batches, which shows a good industrial application prospect.

3. Thermal Stability Comparison Between the Immobilized Enzymes and the Free Enzymes The temperatures of the immobilized enzymes and the free enzymes are kept at different temperatures (30-80° C.) for 1 h, and the remaining enzyme activity at respective optimum reaction temperatures and respective optimum pH is measured with the respective highest enzyme activity as 100%, wherein the result is shown in FIG. 2.

Figure 2:
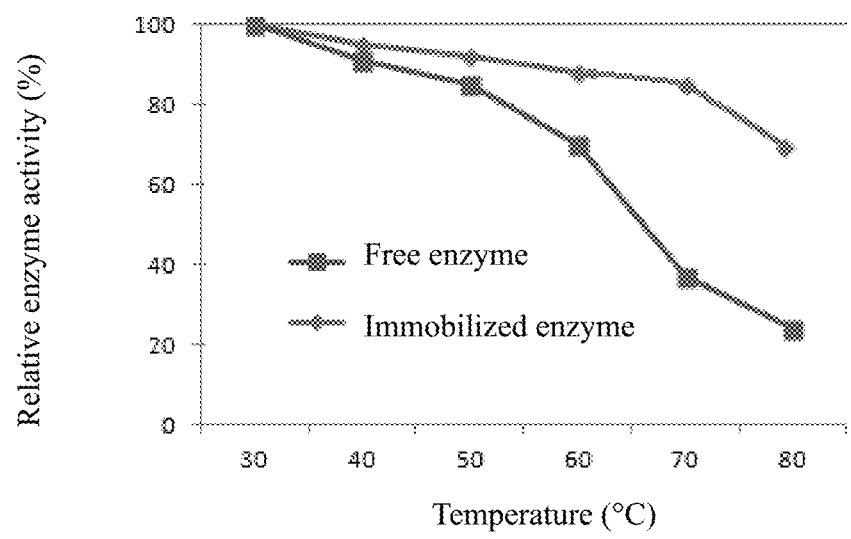
FIG. 2 is a thermal stability comparison diagram of immobilized enzymes and free enzymes of an embodiment of the present invention.

The result is shown in FIG. 2, the thermal stability of the immobilized enzymes is significantly improved with respect to the free enzymes, after the treatment for 60 min at 70° C., the immobilized enzymes remain the relative enzyme activity higher than 85%; while the free enzymes are stable at 50° C. or below, but the relative enzyme activity begins to drop greatly when the temperature is above 50° C.

It should be understood that these embodiments are only used for explaining the present invention and are not intended to limit the scope of protection of the present invention. In addition, it should be further understood that various modifications, adaptations and/or variations of the present invention may be made by those skilled in the art after reading the technical content of the present invention, and all these equivalent forms also fall within the scope of protection as defined by the claims attached to the present invention.

What is claimed is:

1. A method for preparing salidroside, comprising the following steps:
   (1) adding β-glucosidase into a phosphate and/or citrate buffer solution, adding polyacrylamide cross-linked hollow $CoFe_2O_4$ particles, adding a settling agent, glutaraldehyde and sodium borohydride after oscillating, centrifuging same at 320-480 rpm for 5-10 min, feeding same into a thermostatic water bath at 40-45° C., keeping the temperature and stirring same for 1-2 h, discharging, and collecting precipitates to obtain a β-glucosidase cross-linked aggregate;

(2) adding β-D-glucose and tyrosol into a solvent, adding the buffer solution and the β-glucosidase cross-linked aggregate obtained in the step (1), and reacting to obtain a reaction solution; and (3) filtering the reaction solution obtained in the step (2), and carrying out reduced pressure distillation on a filtrate to obtain a crude product; and recrystallizing the crude product to obtain the salidroside.

2. The method for preparing the salidroside according to claim 1, wherein a method for preparing the polyacrylamide cross-linked hollow $CoFe_2O_4$ particles comprises the following steps:

(1) adding 1-2 parts by weight of ammonium persulfate into deionized water which is 20-30 times of the weight of the ammonium persulfate, and uniformly stirring same; and (2) adding 40-45 parts by weight of methyl methacrylate into the deionized water which is 5-8 times of the weight of the methyl methacrylate, uniformly stirring same, feeding same into a reaction kettle, introducing nitrogen, regulating the temperature of the reaction kettle to 60-75° C., keeping the temperature and stirring same for 3-5 h, discharging, cooling, adding 300-500 parts by weight of 0.8-1 mol/l ferric nitrate solution and 200-240 parts by weight of 1.7-2 mol/l cobalt nitrate solution, uniformly stirring same, adding citric acid, adjusting the pH to 3-4, heating same with steam at 100-110° C. until water is dried, discharging, feeding same into a sintering furnace, calcining same at 500-550° C. for 2-3 h, discharging and cooling, feeding same into an acetone solution, soaking at 60-70° C. for 100-110 min, discharging, drying, blending same with 0.3-0.4 parts by weight of sodium persulfate, 20-25 parts by weight of acrylamide and 5-7 parts by weight of calcium chloride, uniformly stirring same, adding the mixture into the deionized water which is 10-20 times of the weight of the mixture, feeding same into the reaction kettle, introducing the nitrogen, regulating the temperature of the reaction kettle to 70-80° C., keeping the temperature and stirring same for 3-5 h, discharging, feeding a product into a drying oven, carrying out vacuum drying at 90-100° C. for 3-5 h, and discharging and cooling to obtain the polyacrylamide cross-linked hollow $CoFe_2O_4$ particles.

3. The preparation method according to claim 1, wherein in the step (1), the β-glucosidase is selected from prune seed β-glucosidase or black plum seed β-glucosidase, and the settling agent is dioxane.

4. The preparation method according to claim 1, wherein in the step (1), a mass ratio of the β-glucosidase to the polyacrylamide cross-linked hollow $CoFe_2O_4$ particles is 1:0.5-1.2.

5. The preparation method according to claim 1, wherein in the step (1), the pH value of the phosphate and/or citrate buffer solution is 5.0-6.0.

6. The preparation method according to claim 1, wherein in the step (2), the solvent is dioxane, tetrahydrofuran, dimethyl sulfoxide or dimethyl formamide.

7. The preparation method according to claim 1, wherein in the step (2), a molar ratio of the β-D-glucose to the tyrosol is 1:1-1.5.

8. The preparation method according to claim 1, wherein in the step (1), the buffer solution is a phosphate-citric acid buffer solution, a sodium citrate-citric acid buffer solution, a sodium dihydrogen phosphate-citric acid buffer solution, a sodium dihydrogen phosphate-phosphoric acid buffer solution, a disodium hydrogen phosphate-citric acid buffer solution or a disodium hydrogen phosphate-phosphoric acid buffer solution.

9. The preparation method according to claim 1, wherein in the step (2), the reaction temperature is 25-70° C., and the reaction time is 6-16 h.

10. The preparation method according to claim 1, wherein in the step (3), the recrystallization solvent is n-hexane-methanol or n-hexane-ethanol.

\* \* \* \* \*